(12) United States Patent
Davis

(10) Patent No.: US 10,241,052 B1
(45) Date of Patent: Mar. 26, 2019

(54) STIMULATED RAMAN SCATTERING IN THE ATMOSPHERE FOR WAVEFRONT CLEAN-UP AND TURBULENCE COMPENSATION OF HIGH-ENERGY LASER BEAMS

(71) Applicant: BOOZ ALLEN HAMILTON INC., McLean, VA (US)

(72) Inventor: James A. Davis, San Diego, CA (US)

(73) Assignee: BOOZ ALLEN HAMILTON INC., McLean, VA (US)

( * ) Notice: Subject to any disclaimer, the term of this patent is extended or adjusted under 35 U.S.C. 154(b) by 0 days.

(21) Appl. No.: 16/040,733

(22) Filed: Jul. 20, 2018

(51) Int. Cl.
  *G01J 3/44* (2006.01)
  *G01N 21/65* (2006.01)

(52) U.S. Cl.
  CPC .............. *G01N 21/65* (2013.01); *G01J 3/44* (2013.01); *G01N 2021/655* (2013.01); *G01N 2201/0635* (2013.01); *G01N 2201/06113* (2013.01)

(58) Field of Classification Search
  CPC ............ G01N 21/65; G01N 2021/655; G01N 2201/06113; G01N 2201/0635; G01J 3/44
  See application file for complete search history.

(56) References Cited

U.S. PATENT DOCUMENTS

| 7,177,021 | B2 * | 2/2007 | Wang ........................ | G01J 3/10 356/301 |
| 2002/0114555 | A1 * | 8/2002 | Seydnejad ............. | G01N 21/65 385/15 |
| 2011/0222054 | A1 * | 9/2011 | Krishnamachari ....... | G01J 3/02 356/301 |
| 2013/0293882 | A1 * | 11/2013 | Dottery ..................... | G01J 3/44 356/301 |

OTHER PUBLICATIONS

R. McCrory, "Raman Scattering of High-Power Lasers in Air," Advanced Technology Developments, LLE Review, Oct. 1, 1991-Sep. 30, 1992, pp. 211-223, vol. 52.
S. Aparanji et al., "Raman Based Power Combining and Wavelength Conversion of High Power Ytterbium Fiber Lasers," Proceedings of SPIE, Fiber Lasers XV: Technology and Systems, Feb. 26, 2018, pp. 105121U-1-105121U-6, vol. 10512, doi:10.1117/12.2290347.

(Continued)

*Primary Examiner* — Dominic J Bologna
(74) *Attorney, Agent, or Firm* — Buchanan Ingersoll & Rooney PC (57) ABSTRACT

An optical system includes a first light source configured to generate a first light beam having a first power. The optical system includes a second light source configured to generate at least one second light beam having a second power. The second power can be greater than the first power. The optical system includes a device for a least partially co-aligning the at least one second light beam of the second power with the first light beam of the first power in a parallel or near-parallel pattern and within a region of atmospheric space so that energy will transfer from photons of the at least one second light beam of the second power to photons of the first light beam of the first power within the region of atmospheric space via Stimulated Raman Scattering (SRS).

20 Claims, 4 Drawing Sheets

(56) References Cited

OTHER PUBLICATIONS

D. Crawford et al., "Advancements of Ultra-High Peak Power Laser Diode Arrays," Proceeding of SPIE, High-Power Diode Laser Technology XVI, Feb. 19, 2018, pp. 105140H-1-105140H-10, vol. 10514, doi: 10.1117/12.2294046.

A.E. Dangor et al. "Forced Raman Scattering in Air by a Two-Frequency Laser Beam." J. Phys. B: At. Mol. Opt. Phys., pp. 797-805, vol. 22.

J. Fukumoto et al.; "Periodically Poled LiNbO3 Optical Parametric Oscillator with Intracavity Difference Frequency Mixing," OSA TOPS, Optical Society of America, Advanced Solid State Lasers, Walter R. Bosenberg and Martin M. Fejer (eds.), 1998, pp. 245-248.

M. Henesian et al.; "Summary of Stimulated Raman Scattering Experiments in the NOVA Air-Path and Projected NOVA and NOVA II System Performance Limits," Lawrence Livermore National Laboratory, UCRL-TR-234110, Aug. 29, 2007. (30 pages).

N.A. Kurnit, "Calculation and Measurement of Stimulated Rotational Raman Scattering in Atmospheric Oxygen," Los Alamos National Laboratory, LA-UR-95-4145, Jan. 1995. (8 pages).

J. Lampel et al., "The Impact of Vibrational Raman Scattering of Air on DOAS Measurements of Atmospheric Trace Gases," Atmospheric Measurement Techniques, 2015, pp. 3767-3787, vol. 8, www.atmos-meas-tech.net/8/3767/2015/ doi:10.5194/amt-8-3767-2015.

P.N. Malevich et al.; "Ultrafast-Laser-Induced Backward Stimulated Raman Scattering for Tracing Atmospheric Gases," Optical Express, EPJ Web of Conferences DOI: 10.1051/ epjconf 201/41 34112009 12009, Aug. 13, 2012, vol. 20, No. 17. (11 pages).

G. McConnell et al., "Simultaneous Stimulated Raman Scattering Second Harmonic Generation in Periodically Poled Lithium Niobate," Optics Express, 2005. (7 pages).

A. Oklopčić et al.; "Raman Scattering by Molecular Hydrogen and Nitrogen in Exoplanetary Atmospheres," The Astrophysical Journal, 832:30 (17pp), 2016 Nov. 20, 2016, pp. 1-17, vol. 832, No. 30, doi:10.3847/0004-637X/832/1/30.

H. Ory et al. "Rayleigh and Raman Scattering in Molecular Nitrogen." RAND Memorandum RM-4664-ARPA, Aug. 1965. (30 pages).

J.R. Peñano et al., "Stimulated Raman Scattering of Intense Free-Electron Laser Radiation in the Atmosphere," Journal of Directed Energy, 1, Spring 2004, 143-159.

M. Rokni et al., "Stimulated Rotational Raman Scattering in the Atmosphere," IEEE Journal of Quantum Electronics, pp. 1102-1108, vol. QE-22, No. 7, Jul. 1986.

T.H. Russell et al.; "Incoherent beam combining using stimulated Brillouin scattering in multimode fibers" Optics Express, Feb. 12, 2001, pp. 246-254, vol. 8, No. 2.

T.H. Russell, "Laser Intensity Scaling Through Stimulated Scattering in Optical Fibers"; Air Force Institute of Technology, Dissertation, Dec. 2001. (206 pages).

R. Van Deelen, "Rotational Raman scattering in the Earth's atmosphere—Modeling and application to satellite measurements of backscattered sunlight," Thesis for SRON—Netherlands Institute for Space Research, Nov. 27, 2007. (181 pages).

F. Vogt et al.; "Detection and Implications of Laser-Induced Raman Scattering at Astronomical Observatories," Phys. Rev., Jun. 23, 2017, pp. 1-17.

C. Yu et al., "All-Glass Fiber Amplifier Pumped by Ultra-High Brightness Pump," Proceedings of SPIE, Fiber Lasers XIII: Technology, Systems, and Applications, Mar. 9, 2016, pp. 972806-1-972806-6, vol. 9728, doi: 10.1117/12.2211134.

\* cited by examiner

STIMULATED RAMAN SCATTERING IN THE ATMOSPHERE FOR WAVEFRONT CLEAN-UP AND TURBULENCE COMPENSATION OF HIGH-ENERGY LASER BEAMS

FIELD

Optical systems and methods are disclosed that involve co-aligning light beams in a region of atmospheric space to transfer energy from one light beam to another via a Stimulated Raman Scattering (SRS) process.

BACKGROUND INFORMATION

The effectiveness of propagating optical energy through the atmosphere from a High-Energy Laser (HEL) source for long distances can be based on the ability to maintain maximum irradiance on a specified area at the target location. This propagation efficiency is degraded by many factors, including: molecular absorption and scattering, aerosol scattering and absorption, atmospheric turbulence, thermal blooming (from absorption and heating of the air), jitter of the optical axis, power and beam quality losses of the HEL source, and limits for any compensation technologies to correct for these phenomena. Adaptive optics processes can be used to correct and mitigate the degradation of propagation efficiency. Known Adaptive optics processes use a measurement of the optical aberrations along an optical path to generate a conjugate phase that is launched from the HEL source. As the HEL wavefront propagates through the turbulent atmosphere, the phase conjugation signal is "undone" by the turbulence and other aberrations, resulting in a correction to the HEL wavefront to provide a wavefront having flat phase front at the target and having high irradiance at the target.

Known adaptive optics elements in HEL systems employ components such as deformable mirrors that are shaped by actuators to generate a surface that modifies the wavefront phase of the laser source for producing a mathematical conjugate of the measured aberration along the propagation path in the atmosphere. These deformable mirrors and other components can be expensive, involve requirements for high level of optical cleanliness, and can be subject to optical and electrical damage. This can be particularly so for adaptive optics systems designed for high energy light beams. The elimination of these costly elements can provide significant cost savings, potentially better performance, improved system reliability and maintainability, and more compact, lightweight packaging. In addition, the limitations of the known adaptive optics designs in terms of spatial resolution, actuator/control loop bandwidth, and servo electronics prevent standard design approaches from compensating for fine-grained, high temporal frequency fluctuations along the optical path.

Optical systems and methods are known from the following, all of which are incorporated herein by reference in their entireties:

Robert L. McCrory, Director, "Raman Scattering of High-Power Lasers in Air," published in the LLE Review, Oct. 1, 1991-Sep. 30, 1992, Volume 52, pp. 211-223.

Aparanji, Santosh, et al., "Raman Based Power Combining and Wavelength Conversion of High Power Ytterbium Fiber Lasers," Proc. SPIE 10512, Fiber Lasers XV: Technology and Systems, 105121U (26 Feb. 2018); doi: 10.1117/12.2290347

Crawford D., P. Thiagarajan, J. Goings, B. Caliva, S. Smith, R. Walker, "Advancements of Ultra-High Peak Power Laser Diode Arrays," Proc. SPIE 10514, High-Power Diode Laser Technology XVI, 105140H (19 Feb. 2018); doi: 10.1117/12.2294046

Dangori, A. E., et al. "Forced Raman Scattering in Air by a Two-Frequency Laser Beam." J. Phys. B: At. Mol. Opt. Phys. 22 (1989) 797-805.

Fukumoto, Joseph M., et al.; "Periodically Poled LiNbO3 Optical Parametric Oscillator with Intracavity Difference Frequency Mixing," OSA TOPS Vol. 19 Advanced Solid State Lasers Walter R. Bosenberg and Martin M. Fejer (eds.) 01998 Optical Society of America.

Henesian, Mark, et al.; "Summary of Stimulated Raman Scattering Experiments in the NOVA Air-Path and Projected NOVA and NOVA II System Performance Limits," UCRL-TR-234110, Aug. 29, 2007.

Kurnit, N. A.; "Calculation and Measurement of Stimulated Rotational Raman Scattering in Atmospheric Oxygen," Los Alamos National Laboratory, LA-UR-95-4145, January 1995.

Lampel, J.; "The Impact of Vibrational Raman Scattering of Air on DOAS Measurements of Atmospheric Trace Gases," Atmos. Meas. Tech., 8, 3767-3787, 2015 www.atmos-meas-tech.net/8/3767/2015/doi:10.5194/amt-8-3767-2015.

Malevich, P. N., et al.; "Ultrafast-Laser-Induced Backward Stimulated Raman Scattering for Tracing Atmospheric Gases," EPJ Web of Conferences DOI: 10.1051/epjconf 201/41 34112009 12009 (2013)

McConnell, Gail, et al.; "Simultaneous Stimulated Raman Scattering Second Harmonic Generation in Periodically Poled Lithium Niobate," Optics Express 2005.

OklopČiČ, Antonija, et al.; "Raman Scattering by Molecular Hydrogen and Nitrogen in Exoplanetary Atmospheres," The Astrophysical Journal, 832:30 (17pp), 2016 November 20 doi:10.3847/0004-637X/832/1/30

Ory, Horsoe A., & Yura, Harold T.; "Rayleigh and Raman Scattering in Molecular Nitrogen." RAND Memorandum RM-4664-ARPA, August 1965.

Penano, J. R., et al.: "Stimulated Raman Scattering of Intense Free Electron Laser Radiation in the Atmosphere," Journal of Directed Energy, 1, Spring 2004, 143-159.

Rokni, Mordechai, & Flusberg, Allen; "Stimulated Rotational Raman Scattering in the Atmosphere," IEEE Journal Of Quantum Electronics, VOL. QE-22, NO. 7, JULY 1986.

Russell, T. H., et al.; "Incoherent beam combining using stimulated Brillouin scattering in multimode fibers;" OPTICS EXPRESS; 12 Feb. 2001/Vol. 8, No. 2.

Russell, T. H.; Laser Intensity Scaling Through Stimulated Scattering in Optical Fibers; Air Force Institute of Technology Dissertation, December 2001.

Van Deelen, Rutger "Rotational Raman scattering in the Earth's atmosphere—Modeling and application to satellite measurements of backscattered sunlight," Thesis for SRON—Netherlands Institute for Space Research, 27 Nov. 2007.

Vogt, Frédéric P. A., et al.; "Detection and Implications of Laser-Induced Raman Scattering at Astronomical Observatories," Phys. Rev. X 7, 021044 (2017).

Yu, Charles X., Oleg Shatrovoy, T. Y. Fan, "All-glass fiber amplifier pumped by ultrahigh brightness pump," Proc. SPIE 9728, Fiber Lasers XIII: Technology, Systems, and Applications, 972806 (9 Mar. 2016); doi: 10.1117/12.2211134.

SUMMARY

An embodiment of an optical system includes a first light source configured to generate a first light beam having a first power; a second light source configured to generate at least one second light beam having a second power, the second power being greater than the first power; and means for a least partially co-aligning the at least one second light beam of the second power with the first light beam of the first power in a parallel or near-parallel pattern and within a region of atmospheric space so that energy will transfer from photons of the at least one second light beam of the second power to photons of the first light beam of the first power within the region of atmospheric space via SRS.

An embodiment of a method for transmitting light beams involves generating a first light beam, the first light beam having a first power; transmitting at least one second light beam having a second power, the second power being greater than the first power; and directing the at least one second light beam of the second power to at least partially co-align with the first light beam of the first power in a parallel or near parallel pattern within a region of atmospheric space to transfer energy from photons of the at least one second light beam of the second power to photons of the first light beam of the first power within the region of atmospheric space via Raman amplification.

An embodiment of an optical system includes a first light source configured to generate a first light beam along an optical path, the first light beam including a first beam outgoing portion and a first beam return portion; means configured for phase conjugating the first beam return portion by imposing an inverse of a detected optical aberration on the first beam outgoing portion to generate a phase conjugated first beam outgoing portion, wherein Stokes-shifted photons from the phase conjugated first beam outgoing portion will form a signal beam having a signal beam wavelength and a signal beam phase; a second light source configured to generate at least one second light beam along the optical path such that pump photons from the at least one second light beam will form a pump beam; means for at least partially co-aligning the pump beam with the signal beam in a region of atmospheric space along the optical path designated as a Raman Interaction Zone (RIZ) which is selected based on its inclusion of gas and or plasma that will facilitate stimulated quantum energy absorption and emission, such that: Stokes-shifted photons of the signal beam will be Stokes-shifted to facilitate stimulated quantum energy absorption and emission by the gas and/or plasma; quantum energy absorption will generate an additional Stokes-shifted photon having the signal beam wavelength and the signal beam phase; and the additional Stokes-shifted photon will amplify the signal beam.

BRIEF DESCRIPTION OF THE DRAWINGS

Other features and advantages of the present disclosure will become more apparent upon reading the following detailed description in conjunction with the accompanying drawings, wherein like elements are designated by like numerals, and wherein.

DETAILED DESCRIPTION

Figure 1:
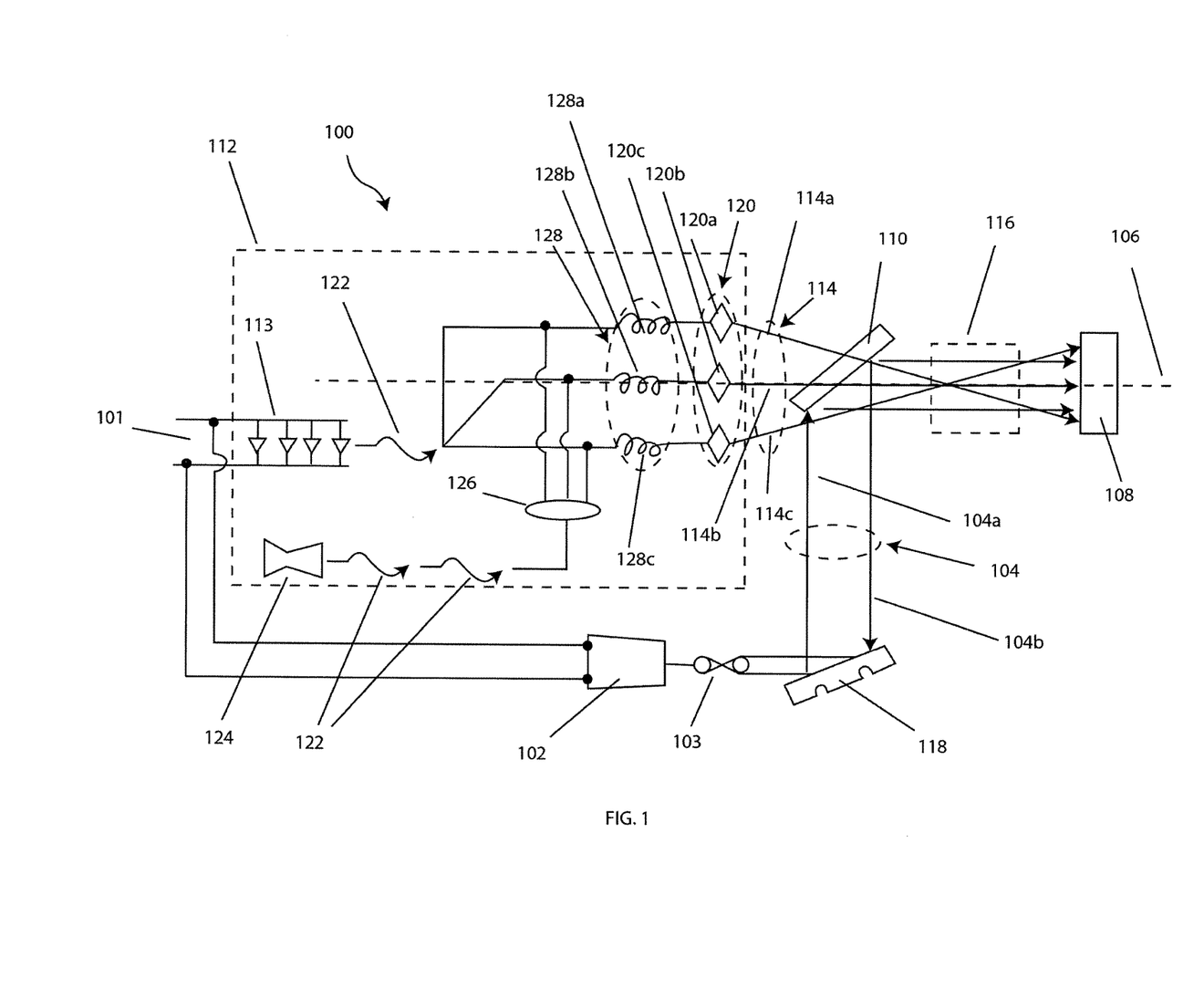
FIG. 1 is an exemplary optical architecture that can be used with an embodiment of the optical system.

Referring to FIG. 1, the optical system 100 can include a first light source 102 configured to generate a first light beam 104 having a first power or a first intensity (intensity being power per unit area). The first light beam 104 may be referred to herein as a signal light beam or a Raman signal. The first light source 102 can be a laser pump source, such as a Raman signal source laser. Exemplary laser sources can be:

Semiconductor diode laser arrays at various wavelengths from ~500-nm to 1100-nm;

Fiber lasers using rare-earth dopants such as Ytterbium (Yb), Neodymium (Nd), Erbium (Er), etc.;

Crystalline Lasers such as Nd:YAG, Yb:YAG, Nd:YLF, Yb:YLF, crystals doped with rare-earth elements, etc.;

Bulk glass lasers, various glass material doped with rare-earth elements, etc.;

Diode-Pumped Alkali Lasers (DPAL) that optically pump alkali vapor atoms with narrow-line diode sources, use of various alkali elements including: Sodium—Na, Potassium—K, Rubidium—Rb, and Cesium—Cs, etc.;

Chemical Lasers that use a chemical reaction to produce optical amplification; and Free Electron Lasers that generate light by propagating a high velocity electron beam through an undulating magnetic field to produce "Synchrotron Radiation" at various wavelengths.

The first light source 102 can be configured to generate the first light beam 104 having a wavelength within a range from the ultra-violet (e.g., at or near 240 nm) to the near infra-red (e.g., at or near 1600 nm). The first light beam 104 can be directed along an optical path 106. The optical path 106 can be a path leading to a target 108. In exemplary embodiments, a beam director 110 can direct the first light beam 104 along the optical path 106, which can include directing the first light beam 104 so as to be incident upon a target 108. The beam director 110 can be any one or combination of a mirror, a lens, a prism, a diffraction grating, a beam splitter, etc. Some embodiments of the beam director 110 can include use of a mechanical mirror-based gimbal, a beam-director unit, a rotating mirror galvanometer mechanism, a Risley prism assembly, phased-array optical assembly, a micro-mirror based microelectromechanical systems (MEMS), etc.

The optical system 100 can include a second light source 112 configured to generate at least one second light beam 114 having a second power or a second intensity (intensity being power per unit area). The second power or second intensity can be greater than the first power or first intensity. The second light beam 114 may be referred to herein as a pump light beam. The second light source 112 can be a laser pump source, such as a high-efficiency laser. The second light source 112 can be any one or combination of a high-power diode array, a diode-pumped solid-state laser, a diode-pumped fiber laser, a diode-pumped alkali laser, etc. Exemplary laser sources can be:

Yb:glass fiber or bulk disk with THG to make shorter wavelengths—360-nm;

K-DPAL with SHG—385-nm;

Rb-DPAL with SHG—397-nm;
Cs-DPAL with SHG—447-nm;
Yb:YAG with SHG—515-nm;
Nd:YAG with SHG—532-nm; and
Yb Fiber with SHG—520-nm to 540-nm.

The second light source 112 can generate a second light beam 114 having a wavelength within a range from the ultra-violet (e.g., at or near 240 nm) to the near infrared (e.g., at or near 1600 nm). In exemplary embodiments, the wavelength of the second light beam 114 can be shorter than the wavelength of the first light beam 104. For example, the wavelength of the second light beam 114 can be within the infrared but at or near the visible light spectrum (e.g., around 700 nm to 800 nm), and the wavelength of the first light beam 104 can be within the infrared or near infrared spectrum (e.g., around 750 nm to 1065 nm). The second light beam 114 can be directed along the optical path 106. For example, the beam director 110 can direct the second light beam 114 along the optical path 106, which can include directing the second light beam 114 to be incident upon the target 108. In exemplary embodiments, the beam director 110 can be configured to direct both the first light beam 104 and the second light beam 114 along the optical path 106, which can include directing both the first light beam 104 and the second light beam 114 so that both are made to be incident on the target 108.

The optical system 100 can include means 110 for a least partially co-aligning the at least one second light beam 114 of the second power with the first light beam 104 of the first power in a parallel or near-parallel pattern and within a region of atmospheric space 116 so that energy will transfer from photons of the at least one second light beam 114 of the second power to photons of the first light beam 104 of the first power within the region of atmospheric space 116 via (SRS) or Raman amplification. The parallel pattern can include the at least one second light beam 114 being coaxial with the first light beam 104. The at least one second light beam 114 being near parallel to the first light beam 104 can include propagating at an angle relative to the first light beam's direction of propagation that is within a range from >0 degrees to 45 degrees (e.g., within a range from >0 degrees to 10 degrees). In exemplary embodiments, the means 110 can be the beam director 110. The SRS facilitates energy conversion from the second light beam 114 to the first light beam 104. In other words, the system 100 can cause the first light beam 104 and the second light beam 114 to propagate in the region of atmospheric space 116 so that energy transfers from the higher-power, short-wavelength second light beam 114 to the lower-power, long-coherence first light beam 104. The region of atmospheric space 116 can be within or at least partially within the optical path 106.

Within the region of atmospheric space 116, a quantum exchange of energy occurs via SRS so that the wavelength of the second light beam 114 is either red-shifted (e.g., shifted to a longer wavelength) in a Stokes shift or blue shifted (e.g., shifted to a shorter wavelength) in an anti-Stokes shift. The magnitude of the quantum shift can be dependent upon a change in quantum state of the molecule(s) and/or atom(s) within the region of atmospheric space 116 that are involved in the SRS process.

The first light beam 104 can be phase conjugated using an adaptive optics technique or coherent, phased array techniques. This can be done before the first light beam 104 and the second light beam 114 are caused to co-align within the region of atmospheric space 116. Phase conjugating a lower-power, long-coherence light beam involves less energy, resources, and sophisticated equipment than phase conjugating a higher-power light beam. It should be noted that known optical systems only use one type of beam (the higher-power light beam), and they phase conjugate this higher-power light beam. This not only requires more energy, resources, and sophisticated equipment, but it also limits known systems to the use of higher-power light beams having longer wavelengths (e.g., in the near infrared spectrum) and better beam quality. With the disclosed system 100 and methods, the first light beam 104 (lower-power light beam having better beam quality) can be phase conjugated and then amplified by energy transfer from the second light beam 114 (the higher-power light beam of poorer beam quality). In addition, the disclosed system 100 is not limited to the use of higher-power light beams with longer wavelengths. For example, the system 100 can be configured to use a potassium alkali diode pump laser as the second light source 112 to generate the second light beam 114 having a wavelength at or near 766 nm. Known optical systems are not able to use a high-powered light beam at or near 766 nm and propagate the light beam to a target 108 with the same beam quality as the disclosed system 100 can.

While shorter wavelengths of the second light beam 114 may be desired, care should be taken to not use wavelengths that would cause the second light beam 114 to be rapidly absorbed by the medium through which it will propagate. For example, when propagating through a medium that includes the earth's atmosphere, aerosols, carbon dioxide, water, etc. may be some constituents that would absorb the second light beam 114, and thus the selection of the wavelength of the second light beam 114 should take this into account. In addition, shorter, ultra-violet wavelengths can cause dissociation and ionization of gases in the atmosphere that will rapidly absorb and attenuate the optical energy in a high-power laser beam.

In exemplary embodiments, each of the first light beam 104 and the second light beam 114 can be tuned to a single wavelength. Alternatively, a band of wavelengths can be used. It is contemplated that the narrower the bandwidth, the more efficient the Raman conversion will be during the SRS process. For example, for a fiber laser system, a bandwidth on the order of 10-GHz can be used. Making the linewidth narrower than 10-GHz can lead to undesirable, nonlinear behaviors in the glass fibers themselves.

It is also contemplated for the polarization of each of the first light beam 104 and the second light beam 114 to be tuned to maximize efficiency of the Raman conversion process. The polarization purity or Polarization Extinction Ratio (PER) is the ratio of the energy in a preferred linear polarization state vs. the energy not in that preferred state. PER between 10-dB (90% in the correct polarization state) to 20-dB (99% in the correct polarization state) can be used. For a fiber laser system, this can correspond to 15-dB PER.

In exemplary embodiments, the region of atmospheric space 116 can include a predetermined amount of gas and/or plasma capable of facilitating stimulated quantum energy absorption and emission. The term atmospheric should not be interpreted as being limited to gas and/or plasma at or near the earth. Any region of space (e.g., atmospheres of other planets, free floating gas and/or plasma formations in space, etc.) can include gas and/or plasma capable of facilitating stimulated quantum energy absorption and emission. The gas and/or plasma can include a predetermined amount of nitrogen, oxygen, hydrogen, methane, carbon dioxide, etc. The predetermined amount of gas and/or plasma can be defined as a threshold density of the gas or the plasma that will generate adequate SRS so as to achieve the desired amplification of the first light beam 104. For example, for air at sea level the molecular number density is $2.69 \times 10^{19}$ molecules/cm$^3$. Nitrogen makes up 78% of air, giving $\sim 2.1 \times 10^{19}$ molecules/cm$^3$; oxygen at 21% of air is $0.565 \times 10^{19}$ molecules/cm$^3$. Air density declines rapidly with altitude, dropping by half at 6.65-km ($\sim$22,000 feet) altitude. A threshold range for nitrogen can be 1 to $2.15 \times 10^{19}$ molecules/cm$^3$, and a threshold range for oxygen can be 2.5 to $5.6 \times 10^{18}$ molecules/cm$^3$. A preferred range for nitrogen can be 0.2 to $2.1 \times 10^{19}$ molecules/cm$^3$ and a preferred range for oxygen can be 0.05 to $0.565 \times 10^{19}$ molecules/cm$^3$.

It will be understood that the stimulated quantum energy absorption and emission can work at lower densities by adjustment of the distance by which the first light beam 104 and the second light beam 114 are caused to co-align. For example, as the density of the gas and/or plasma decreases, the longer the distance within which the first and second light beams 104, 114 are co-aligned can be used to allow for the desired stimulated quantum energy absorption and emission to take place. The portion of the region of atmospheric space 116 in which SRS provides adequate energy transfer to amplify the first light beam 104 may be referred to herein as the Raman interaction zone (RIZ).

The SRS process within the RIZ can be described in the following manner. Stokes-shifted photons of the first light beam 104 are injected into the second light beam 114 (due to the co-alignment), which causes energy of the pump photons (photons of the second light beam 114) to be absorbed and to undergo a conversion to Stokes-shifted photons. The emission of a Stokes-shifted photon is stimulated by the presence of photons of the first beam 104 and the newly generated Stokes-shifted photons will consequently propagate with the original optical phase of the photons of the first beam 104. With the threshold density of the gas and/or plasma being present, the total Raman-scattering rate is increased beyond that of spontaneous Raman scattering, resulting in photons of the second light beam 114 being converted more rapidly into additional Stokes-shifted photon and leading to SRS. This results in amplification of the first light beam 104 in the presence of the second light beam 114.

In exemplary embodiments, the region of atmospheric space 116 can be a region of earth's atmosphere. For example, the optical path 106 may include passing through a portion of the earth's atmosphere, wherein the system 100 uses that portion as the region of atmospheric space 116. Oxygen and nitrogen are the most plentiful gas molecules in the earth's atmosphere. The SRS shift in oxygen and nitrogen are typically either rotational (involving a quantum change in the rotational energy of the molecules) or vibrational (involving a quantum change in the vibrational state of the molecule). The strongest Raman gain in the earth's atmosphere is a quantum vibrational change from the v=0 state to the v=1 state that occurs on the S (8) line of nitrogen. This quantum energy absorption by the nitrogen molecule can be stimulated by a Stokes-shifted, signal photon (e.g., a Stokes-shifted first light beam 104 photon) to generate a second signal photon of the same wavelength and optical phase. The phase of the original pump photon (e.g., second light beam 114 photon) is not preserved in the process. The generation of the second signal photon of the same wavelength and optical phase amplifies the signal light beam (i.e., amplifies the first light beam 104) and retains the optical phase of the first light beam 104 photon.

In exemplary embodiments, the second power of the second light beam 114 can be at least an order of magnitude greater than the first power of the first light beam 104. While the first power of the first light beam 104 can be any wattage that is lower than that of the second power of the second light beam 114, it is contemplated for the power of the first light beam 104 to be within a range from 1,000 watts to 5,000 watts, and for the second power of the second light beam 114 to be within a range from 10,000 watts to 2,000,000 watts.

In exemplary embodiments, the first light source 102 can be configured to generate the first light beam 104 having a first beam quality. The second light source can be configured to generate the at least one second light beam 114 having a second beam quality. For example, the first beam quality can have at least one of spot size, beam divergence, beam propagation, and beam transformation that is more enhanced than that of the second beam quality. Beam quality can include any one or combination of measures and factors, including but not limited to Beam Parameter Product (BPP), $M^2$, power-in-the-bucket, Strehl ratio, beam width, E-field beam profile, etc. Beam quality can also be affected by jitter in the components of the optical system 100 (e.g., the more jitter, the poorer the beam quality). What is considered better beam quality as opposed to poorer beam quality may depend on the application for the light beam. For example, some applications benefit more from a better beam width, while other applications benefit more from a $M^2$ being close to unity. In an exemplary embodiment, the beam quality of the first light beam 104 can be within a range from $1.0 \leq M^2 \leq 1.5$. The beam quality for the second light beam 114 can be within a range from $1.5 \leq M^2 \leq 15.0$.

The system 100 can be configured to phase conjugate the first light beam 104 (having lower power, longer wavelength, and better beam quality), which requires less energy and resources. The system 100 can then amplify the phase conjugated first light beam 104 via a SRS process that transfers energy from the second light beam 114 (having higher power, shorter wavelength, and poorer beam quality). With known systems, the higher-powered beam must have a better beam quality, which adds to the difficulty and complexity of the optical system. With the disclosed system 100, the second light beam 114 need only have a beam quality that allows it to propagate along the optical path 106 and into the region of atmospheric space 116, which can include propagating into the RIZ.

In exemplary embodiments, the first light source 102 can be configured to generate and transmit a phase conjugated light beam as part of the first light beam 104. For example, an adaptive optics technique can be used to phase conjugate the first light beam 104. This can be done before the first light beam 104 and the second light beam 114 are caused to co-align within the region of atmospheric space 116. In exemplary embodiments, this can be done before the first light beam 104 is directed along the optical path 106. In a non-limiting, exemplary embodiment, an adaptive optics technique can be used to reduce the effect of wavefront distortions (e.g., caused by the light beam propagating through a medium) in the first light beam 104 by measuring the distortions in the wavefront of the first light beam 104 and actuating an optical element (e.g., deforming a mirror) to compensate for the distortions. The optical aberrations can be measured by sampling a portion of light reflected by the target 108, backscattered light in the vicinity of the target 108, or any desired location in between. This light can have the information on the intervening atmospheric turbulence and optical distortions. This returning optical beam can be collected back at the first light beam source 102 where it is measured, and a phase conjugate is either calculated by a mathematical inversion of the optical matrix or it is generated by other non-linear processes. This phase conjugate is then imposed on the phase conjugator 118 to modify the out-going portion of the first light beam. Alternatively, in embodiments in which the first light beam 104 is a plurality of light beams, the phase conjugate may be used to control the optical parameters in a phased array of "beamlets" that are coherently combined by electro-optical means.

While embodiments may disclose and illustrate the first light beam 104 as being a single light beam, it is contemplated for the first light source 102 to be configured to generate a single first light beam 104 or a plurality of first light beams 104. With the first light beam 104 being a single light beam, the first light beam 104 can be phase conjugated by a deformable mirror or other non-linear phase conjugating process. With the first light beam 104 being a plurality of light beams, the turbulence compensation and improvement in the beam quality can be accomplished using a phase array of smaller beams that are coherently combined and phase conjugated by adjusting the phases of the individual "beamlets."

In an exemplary embodiment, the optical element can be configured to generate tip-tilt correction movements, which are translated to the tilts of the distorted wavefront. This can be done to generate a phase conjugation of the first light beam 104, which can be imposed on the first light beam 104 to form the phase conjugated first light beam 104. This phase conjugated first light beam 104 can then be propagated along the optical path 106 (the phase conjugation being an inverse of the optical aberration along the optical path 106), and be caused to co-align with the second light beam 114 for Raman amplification. Methods of amplifying the phase conjugated light beam disclosed herein can improve the irradiance of the light beam (as compared to known systems) on the target 108, even at extended ranges.

In exemplary embodiments, the optical system 100 can include a processor in operative association with a sensor. For example, the processor can be configured to detect an optical aberration generated by a medium through which the first light beam 104 propagates. The processor can be configured to impose a conjugate on the first light beam 104 to generate the phase conjugated light beam. In this regard, processor-sensor configuration can be used as a phase conjugator 118.

In exemplary embodiments, the processor can be configured to sample a portion of the first light beam 104 to detect the optical aberration. For instance, the first light beam 104 can include a first beam outgoing portion 104a (which may be referred to herein as the Raman signal) and a first beam return portion 104b (which may be referred to herein as the Raman beacon). The first beam outgoing portion 104a can be directed so as to propagate through the medium to be incident on the target 108, some other intervening object, or a region of space and reflected back to generate the first beam return portion 104b. In exemplary embodiments, propagating though the medium can include being directed along the optical path 106. The sensor can detect wavefronts of the first light beam 104 and the processor can analyze them to detect wavefront distortions due to the optical aberrations generated by the medium. For example, the sensor can be a pixelated array by which wavefront perturbation can be captured to generate a wavefront map. The processor can calculate the conjugation and the inverse of the detected optical aberration of the medium can be imposed on the first beam outgoing portion 104a to generate a phase conjugated first beam outgoing portion 104a. This can be done by the processor calculating optimal mirror shapes (e.g., the wavefront map can be used to determine which mirrors to be moved or deformed and by how much) to correct for the aberrations. The first light beam 104 has a lower power, and thus the phase conjugation can be done at very low powers by sampling the first beam return portion 104b.

The intervening object or region of space can be any one or combination of: 1) backscatter of the amplified Raman signal hitting the target 108; 2) a separate Raman beacon illuminator laser that is reflected by the target 108 and then separated spectrally (e.g., by a dichroic coating on an optic or dispersive element such as a prism or optical grating); 3) backscatter in the gas and/or plasma by Rayleigh or Raman processes; 4) resonant absorption and re-emission of photons by select quantum states such as those corresponding to the D1 and D2 lines of alkali atoms such as sodium in the upper atmosphere (so-called sodium guidestar adaptive optics). In exemplary embodiments, the beam director 110 can include use of a telescope, wherein the output pupil or exit pupil of the telescope can be used for projection of the first beam outgoing portion 104a and collection of the first beam return portion 104b. The first light source 102 and/or the second light source 112 can be configured to generate a pulsed first light beam 104 and/or a pulsed second light beam 114. With a pulsed operation and use of an optical element having an output pupil, the sample range (sampling for phase conjugation) can be set by a range-gating process in which the "shutter" on a wavefront sensor is timed to correspond with the photon time-of-flight from the output pupil to the sample plane and back to the output pupil.

It is understood that the adaptive optics techniques disclosed herein are for exemplary purposes only and that other adaptive optics systems and methods can be used.

In exemplary embodiments, the means 110 for a least partially co-aligning can be configured to co-align the at least one second light beam 114 with the phase conjugated light beam. The co-aligning can be done to amplify the first light beam 104 via a SRS process. This is in contrast to known systems that phase conjugate a high-powered light beam. With the disclosed system 100, the second light beam 114 (the higher power beam) can be directed along the optical path 106 without being phase conjugated. Energy can be transferred from the second light beam 114 to the phase conjugated first beam (the lower power beam) without the aberrations in the second light beam 114 being imprinted on the first light beam 104. Thus, phase conjugation can be performed on the lower power light beam at lower expenses and with higher reliability, and then the energy from the higher-power second light beam 114 (having low quality) can be transferred to the first light beam 104 to amplify the first light beam 104. The first light beam 104 (after being amplified in the RIZ) can be made to be incident upon the target 108 with a flat phase front at the target 108 and with high irradiance. The system 100 can reduce propagation efficiency degradation, perform beam clean up, and compensate for atmospheric turbulence at the fraction of the cost of known optical systems, but with higher reliability and with a less expenditure of energy.

In exemplary embodiments, the region of atmospheric space can be a volume of space along an optical path 106 of the first light beam 104 and the second light beam 114 with a range from 1 kilometer to 10 kilometers. The portion of the region of atmospheric space 116 in which SRS provides adequate energy transfer to amplify the first light beam 104 is referred to as the RIZ. It is contemplated for the RIZ to be a volume of space that is within the range from 1 kilometer to 10 kilometers for the intended applications of the optical system 100. Alternatively, this range can be from 0.5 kilometers to 100 kilometers. The range can depend on several factors, including the application for which the optical system 100 is being used, the wavelengths and intensities of the light beams, the type and chemical properties (e.g., temperature, pressure, density, etc.) of the gas and/or plasma, other Raman gain factors, etc. For example, it is contemplated that the RIZ would have to increase as the density of the gas and/or plasma decreases, and thus the range of atmospheric space 116 would have to increase. Referring to the example in which the earth's atmosphere is the region of atmospheric space 116, each of the density of oxygen and nitrogen decreases the higher in altitude the region of atmospheric space 116 is located. Thus, it may be so that the range of the region of atmospheric space 116 would have to be increased as the altitude the region of atmospheric space 116 lies is increased.

Figure 2:
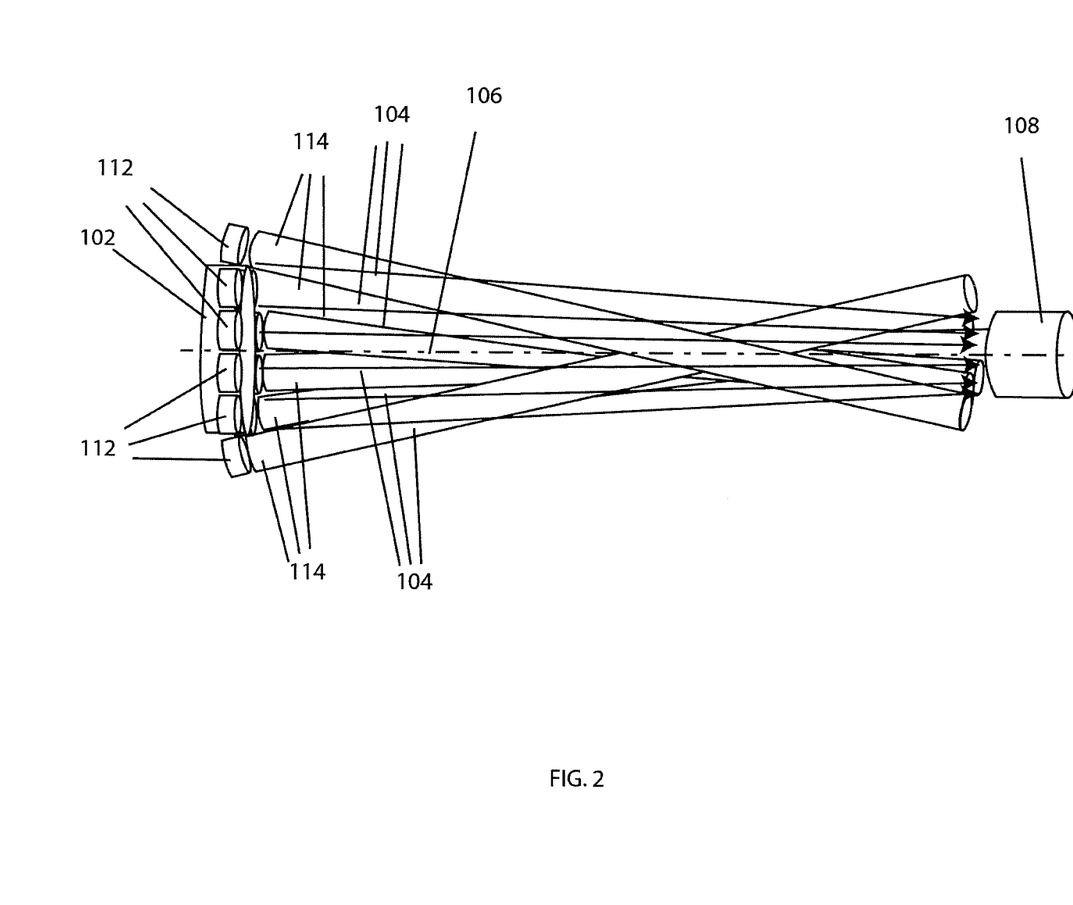
FIG. 2 is an exemplary side view of a Raman signal and a plurality of pump light beams propagating along an optical path that can be generated by an embodiment of the optical system.

Referring to FIG. 2, the range of the region of atmospheric space 116 not only depends on the physical volume or expanse of the gas and/or plasma, but also on the co-aligning of the first light beam 104 and the second light beam 114 within the RIZ. The physical volume or expanse of the gas and/or plasma is out of the control of the user of the system 100. But the co-alignment of the first light beam 104 with the second light beam 114, and in particular the range or distance over which they co-align, can be controlled by a user of the system 100. Co-aligning can be defined as causing the second light beam 114 to be coaxial or to form a near-parallel pattern with the first light beam 104.

In exemplary embodiments, the second light source can be configured to generate a plurality of second light beams 114. For example, the second light source 112 can be a multiple photo diode array configured to generate a plurality of second light beams 114. The system 100 can control the co-alignment of the first light beam 104 with the second light beam 114 (or plurality of second light beams 114), and in particular the range or distance over which they co-align. For example, the beam director 110 can include light beam directing elements (e.g., mirrors, lenses, etc.) that can facilitate aiming the first light beam 104 and/or the second light beam 114. With the second light beam 114 being a plurality of second light beams 114, the plurality of second light beams 114 can be directed to propagate along the optical path 106 in a parallel or nearly parallel manner with the optical path 106 or a cross-path manner (meaning entering the optical path 106 at an angle so as to exist within the optical path 106 for a distance and then exiting the optical path 106). With the cross-path propagation, the angle at which each second light beam 114 enters the optical path 106 can be adjusted to adjust the distance each second light beam 114 exists within the optical path 106, and therefore adjust the range of the region of atmospheric space 116 within which the first light beam 104 and the second light beams 114 co-align. The closer the angle of entrance is to being normal to the direction of the optical path 106, the shorter the range or distance the second light beam 114 exists within the optical path 106, and therefore the shorter the range or distance by which the first light beam 104 and the second light beam 114 co-align.

Referring to FIG. 1, in exemplary embodiments, the optical system 100 can include a harmonic generator 120 configured to convert the at least one second light beam 114 to a shorter wavelength. The harmonic generator 120 can include any one or combination of a second harmonic generator or a third harmonic generator. For example, an optical parametric oscillator can be used to convert a light beam into a second light beam 114 having a wavelength that is one-half or one-third of its original wavelength by means of nonlinear optical interaction. For example, a light beam at 1,200-nm wavelength can be converted to a second wavelength of 600-nm by Second Harmonic Generation (SHG) or to a second wavelength of 400-nm by Triple Harmonic Generation (THG) processes. In an exemplary embodiment, the nonlinear optical interaction can be achieved by propagating the second light beam 114 through a medium (e.g., a fiber optic) that induces nonlinear gain. Use of a harmonic generator 120 can be done to tune the efficiency of the system 100. For example, the second light beam 114 can be converted to shorter wavelengths, which may be more beneficial for the Raman conversion process since the Raman gain is proportional to $\lambda^{-4}$.

In exemplary embodiments, the second light source 104 can be configured as a pulsed light beam generator. In addition, the first light source 112 can be configured as a pulsed light beam generator. The Raman gain is a factor that can influence many of the operating parameters of the system 100. The Raman gain can be tuned by adjusting the intensity of the first light beam 104 and/or the second light beam 114. As the intensity is power per unit area, the intensity can be tuned by adjusting the diameter of the light beams and/or by generating light beams of pulsed formats. The smaller the diameter, the greater the intensity. And, using pulsed formats can pack energy into short duration pulses. The shorter the pulse the greater the intensity.

In exemplary embodiments, the first light source 102 can be configured to generate the first light beam 104 exhibiting a first diffractive spread along its optical path 106. The second light source 112 can be configured to generate the at least one second light beam 114 exhibiting a second diffractive spread along its optical path 106. In exemplary embodiments, the second diffractive spread can be greater than the first diffractive spread. The diffractive spread can be a function of beam quality. For example, a light beam of better beam quality may exhibit a lower diffractive spread, whereas a light beam of poorer beam quality may exhibit a higher diffractive spread. The beam quality of the second light beam 114 can be lower than that of the first light beam 104, and thus the system 100 can be configured to generate the first light beam 104 with a diffractive spread that is lower than the diffractive spread of the second light beam 114. One of the ways to decrease the diffractive spread is to increase the light beam diameter at the output pupil 110.

In exemplary embodiments, the first light source 102 can be configured to generate the first light beam 104 to have a first diameter, $D_1$. The second light source can be configured to generate the at least one second light beam 114 to have a second diameter, $D_2$. In exemplary embodiments, the first diameter can be greater than the second diameter. The first light beam 104 having a relatively large diameter can achieve low diffractive spreading along the optical path 106 to the target 108. Because the second light beam 114 need not be of excellent beam quality, the diffractive spread of the higher-power second light beam 114 is not as much of a factor in the efficient operation of the system 100 as the diffractive spread of the lower-power first light beam 104. Thus, unnecessary energy and resources need not be expended on unduly reducing the diffractive spread of the second light beam 114.

Figure 3:
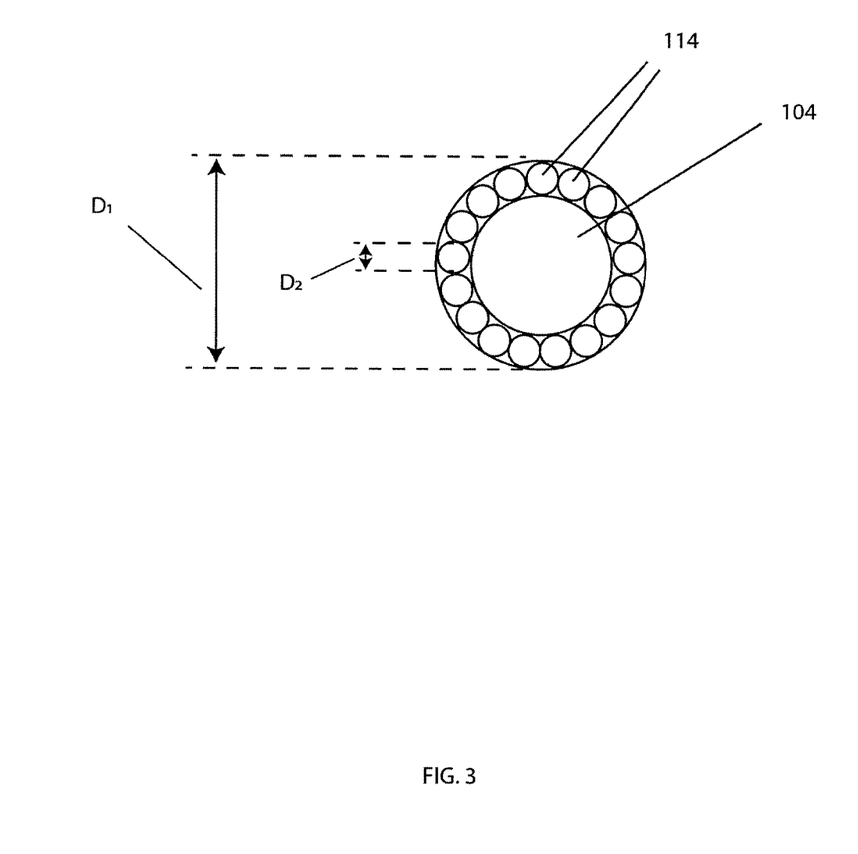
FIG. 3 shows a co-propagation pattern of a Raman signal with a plurality of pump light beams that can be generated by an embodiment of the optical system.
Figure 4:
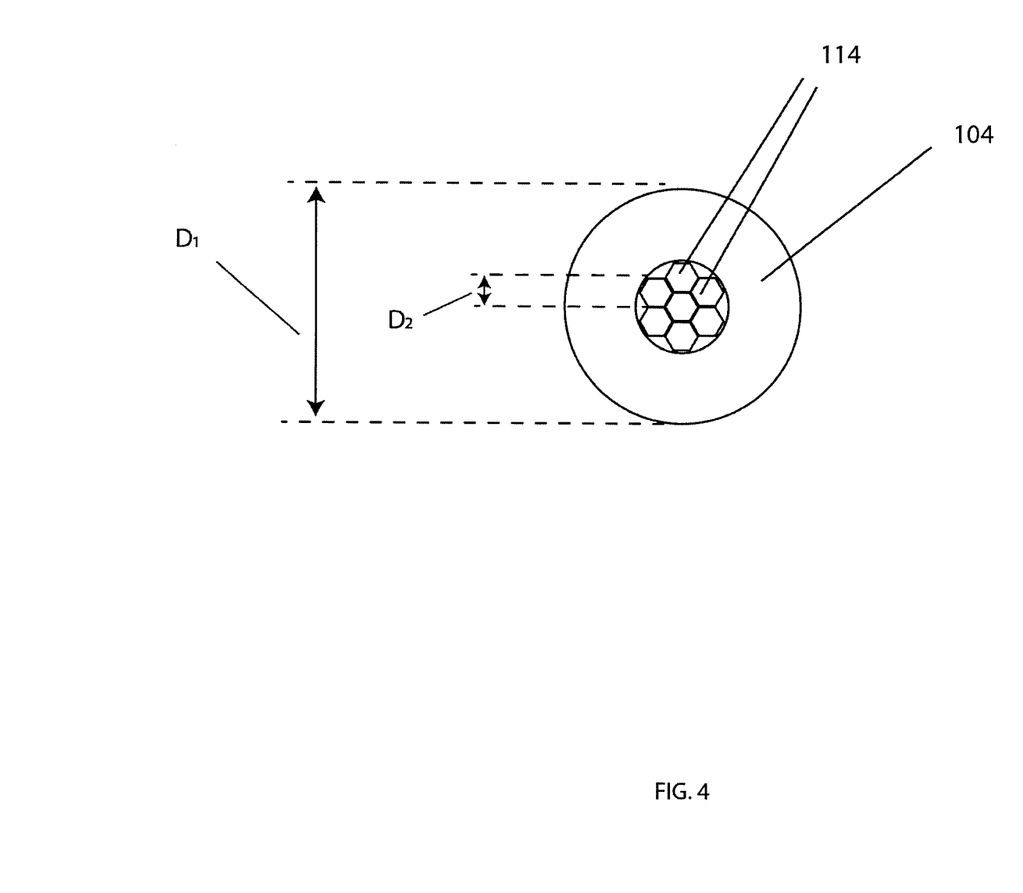
FIG. 4 shows another co-propagation pattern of a Raman signal with a plurality of pump light beams that can be generated by an embodiment of the optical system.

Referring to FIGS. 3-4, the second light source can be configured to generate a plurality of second light beams 114. The means 110 for co-aligning can be arranged to direct the plurality of second light beams 114 so as to be clustered around or within the first diameter of the first light beam 104. Any two or more second light beams 114 can be co-aligned with the first light beam 104 in any number of co-propagation patterns. The propagation pattern can be defined as the position of the second light beams 114 relative to each other and relative to the first light beam 104 as they propagate along the optical path 106, or at least within the RIZ. A light beam profile can be defined herein as the diameter and position of the light beam within the optical path 106 when viewed from a point of view coaxial with the optical path 106. For example, FIGS. 3-4 are views at an angle normal to a cross-section of an optical path 106, the views including the first light beam 104 and second light beams 114 traveling along the optical path 106. The first light beam 104 can have a diameter $D_1$ and be directed along the optical path 106. Each second light beam 114 can have a diameter $D_2$ and each be directed along the optical path 106, $D_2 < D_1$.

FIG. 3 shows a cluster co-propagation pattern in which each second light beam 114 is positioned within $D_1$ but at a periphery of $D_1$. In exemplary embodiments, the plurality of second light beams 114 can form a concentric circle about the periphery of $D_1$, but still being within $D_1$. In other words, each second light beam 114 can be adjacent each other and the plurality of second light beams 114 can follow the arc of the outer diameter, $D_1$, of the first light beam 104. FIG. 4 shows a cluster co-propagation pattern in which each second light beam 114 is positioned within $D_1$ but at or near a center of the first light beam 104. In exemplary embodiments, the plurality of second light beams 114 can be adjacent each other but clustered so as to travel along and/or about a central axis of the first light beam 104.

It is understood that the co-propagation patterns described and illustrated herein are for exemplary purposes only and that other co-propagation patterns can be used.

A method for transmitting light beams can involve generating a first light beam 104, the first light beam 104 having a first power.

The method can involve transmitting at least one second light beam 114 having a second power. The second power can be greater than the first power.

The method can involve directing the at least one second light beam 114 of the second power to at least partially co-align with the first light beam 104 of the first power in a parallel or near parallel pattern within a region of atmospheric space 116 to transfer energy from photons of the at least one second light beam 114 of the second power to photons of the first light beam 104 of the first power within the region of atmospheric space 116 via SRS or Raman amplification.

In exemplary embodiments, the region of atmospheric space 116 can include a predetermined amount of gas and/or plasma capable of facilitating stimulated quantum energy absorption and emission.

In exemplary embodiments, the second power can be at least an order of magnitude greater than the first power.

The method can involve generating the first light beam 104 having a first beam quality. The method can involve generating the at least one second light beam 114 having a second beam quality. For example, the first beam quality can have at least one of spot size, beam divergence, beam propagation, and beam transformation that is more enhanced than that of the second beam quality.

Referring to FIG. 1, an exemplary, non-limiting embodiment of the optical system 100 can include a first light source 102 configured to generate a first light beam 104 along an optical path 106. The first light beam 104 can include a first beam outgoing portion 104a and a first beam return portion 104b.

The optical system 100 can include a means 110 configured for phase conjugating the first beam return portion 104b by imposing an inverse of a detected optical aberration on the first beam outgoing portion 104a to generate a phase conjugated first beam outgoing portion 104a. The detected optical aberration can be one that is generated by a medium through which the first beam outgoing portion 104a propagates. The means 110 can be a phase conjugator 118 and be in electro-optical connection with the first light source 102. In at least one embodiment, the first light beam 104 may be directed through at least one optical amplifier 103 before being sent through the phase conjugator 118.

In exemplary embodiments, Stokes-shifted photons from the phase conjugated first beam outgoing portion can form a signal beam. The signal beam can have a signal beam wavelength and a signal beam phase.

The optical system 100 can include a second light source 112 configured to generate at least one second light beam 114 along the optical path 106 such that pump photons from the at least one second light beam 114 will form a pump beam. The second light source 112 can be a diode laser array 113 in connection with an electrical power source 101, the diode laser array 113 configured to convert electrical power from the electrical power source 101 to optical power in the form of a plurality of second light beams 114. The diode laser array can also be configured to generate a plurality of pulsed second light beams 114. This can be achieved through use of a master oscillator 124. The master oscillator 124 can include at least one optical pump 122 and a beam splitter 126. Each second light beam 114 can be directed through a fiber laser amplifier 128. For example, the system 100 can be configured to generate a first-second light beam 114a, a second-second light beam 114b, and a third-second light beam 114c. The first-second light beam 114a can be directed through a first fiber laser amplifier 128a, the second-second light beam 114b can be directed through a second fiber laser amplifier 128b, the third-second light beam 114c can be directed through a third fiber laser amplifier 128c. In exemplary embodiments, each of the first-second light beam 114a, the second-second light beam 114b, and the third-second light beam 114c can, individually, be directed through an optical pump 122 before or after being sent through their respective amplifiers 128a, 128b, 128c. In exemplary embodiments, each of the first-second light beam 114a, the second-second light beam 114b, and the third-second light beam 114c can, individually, be directed through a harmonic generator 120a, 120b, 120c.

The optical system can include a means 110 for at least partially co-aligning the pump beam with the signal beam in a region of atmospheric space 116 along the optical path 106. The region of atmospheric space 116 can be designated as a Raman Interaction Zone (RIZ). The RIZ can be selected based on its inclusion of gas and/or plasma that will facilitate stimulated quantum energy absorption and emission.

In exemplary embodiments, Stokes-shifted photons of the signal beam will be Stokes-shifted to facilitate stimulated quantum energy absorption and emission by the gas or the plasma.

In exemplary embodiments, quantum energy absorption will generate an additional Stokes-shifted photon having the signal beam wavelength and the signal beam phase.

In exemplary embodiments, the additional Stokes-shifted photon will amplify the signal beam.

It will be understood that modifications to the embodiments disclosed herein can be made to meet a particular set of design criteria. For instance, any of the light sources 102, 104, co-alignment means 110, harmonic generators 120, phase conjugators 118, optical pumps 122, fiber amplifiers 128, or any other component of the system 100 can be any suitable number or type of each to meet a particular objective. Therefore, while certain exemplary embodiments of the system 100 and methods of using the same disclosed herein have been discussed and illustrated, it is to be distinctly understood that the invention is not limited thereto but can be otherwise variously embodied and practiced within the scope of the following claims.

It will be appreciated that some components, features, and/or configurations can be described in connection with only one particular embodiment, but these same components, features, and/or configurations can be applied or used with many other embodiments and should be considered applicable to the other embodiments, unless stated otherwise or unless such a component, feature, and/or configuration is technically impossible to use with the other embodiment. Thus, the components, features, and/or configurations of the various embodiments can be combined together in any manner and such combinations are expressly contemplated and disclosed by this statement.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein. Additionally, the disclosure of a range of values is a disclosure of every numerical value within that range, including the end points.

What is claimed is:

1. An optical system, comprising:
    a first light source configured to generate a first light beam having a first power;
    a second light source configured to generate at least one second light beam having a second power, the second power being greater than the first power; and
    means for a least partially co-aligning the at least one second light beam of the second power with the first light beam of the first power in a parallel or near-parallel pattern and within a region of atmospheric space so that energy will transfer from photons of the at least one second light beam of the second power to photons of the first light beam of the first power within the region of atmospheric space via Stimulated Raman Scattering (SRS).

2. The optical system recited in claim 1, wherein the region of atmospheric space includes a predetermined amount of gas and/or plasma capable of facilitating stimulated quantum energy absorption and emission.

3. The optical system recited in claim 1, wherein the second power is at least an order of magnitude greater than the first power.

4. The optical system recited in claim 1, wherein the first light source is configured to generate the first light beam having a first beam quality and the second light source is configured to generate the at least one second light beam having a second beam quality, the first beam quality having at least one of spot size, beam divergence, beam propagation, and beam transformation that is more enhanced than that of the second beam quality.

5. The optical system recited in claim 1, wherein the first light source is configured to generate and transmit a phase conjugated light beam as part of the first light beam.

6. The optical system recited in claim 5, comprising:
    a processor in operative association with a sensor, the processor being configured to detect an optical aberration generated by a medium through which the first light beam propagates and to impose a conjugate on the first light beam to generate the phase conjugated light beam.

7. The optical system recited in claim 6, wherein the processor is configured to sample a portion of the first light beam to detect the optical aberration.

8. The optical system recited in claim 5, wherein the means for a least partially co-aligning is configured to co-align the at least one second light beam with the phase conjugated light beam.

9. The optical system recited in claim 1, wherein the region of atmospheric space is a volume of space along an optical path of at least one of the first light beam and the second light beam with a range from 1 kilometer to 10 kilometers.

10. The optical system recited in claim 1, wherein the second light source is configured to generate a plurality of second light beams.

11. The optical system recited in claim 1, comprising:
    a harmonic generator configured to convert the at least one second light beam to a shorter wavelength.

12. The optical system recited in claim 1, wherein the second light source is configured as a pulsed light beam generator.

13. The optical system recited in claim 1, wherein the first light source is configured to generate the first light beam exhibiting a first diffractive spread along its optical path, and the second light source is configured to generate the at least one second light beam exhibiting a second diffractive spread along its optical path, the second diffractive spread being greater than the first diffractive spread.

14. The optical system recited in claim 1, wherein the first light source is configured to generate the first light beam to have a first diameter, and the second light source is configured to generate the at least one second light beam to have a second diameter, the first diameter being greater than the second diameter.

15. The optical system recited in claim 14, wherein the second light source is configured to generate a plurality of second light beams, and the means for co-aligning is arranged to direct the plurality of second light beams so as to be clustered around or within the first diameter of the first light beam.

16. A method for transmitting light beams, the method comprising:
    generating a first light beam, the first light beam having a first power;
    transmitting at least one second light beam having a second power, the second power being greater than the first power; and
    directing the at least one second light beam of the second power to at least partially co-align with the first light beam of the first power in a parallel or near parallel pattern within a region of atmospheric space to transfer energy from photons of the at least one second light beam of the second power to photons of the first light beam of the first power within the region of atmospheric space via Raman amplification.

17. The method recited in claim 16, wherein the region of atmospheric space includes a predetermined amount of gas and/or plasma capable of facilitating stimulated quantum energy absorption and emission.

18. The method recited in claim 16, wherein the second power is at least an order of magnitude greater than the first power.

19. The method recited in claim 16, comprising:
generating the first light beam having a first beam quality; and
generating the at least one second light beam having a second beam quality, the first beam quality having at least one of spot size, beam divergence, beam propagation, and beam transformation that is more enhanced than that of the second beam quality.

20. An optical system, comprising:
a first light source configured to generate a first light beam along an optical path, the first light beam including a first beam outgoing portion and a first beam return portion;
means configured for phase conjugating the first beam return portion by imposing an inverse of a detected optical aberration on the first beam outgoing portion to generate a phase conjugated first beam outgoing portion, wherein Stokes-shifted photons from the phase conjugated first beam outgoing portion will form a signal beam having a signal beam wavelength and a signal beam phase;
a second light source configured to generate at least one second light beam along the optical path such that pump photons from the at least one second light beam will form a pump beam;
means for at least partially co-aligning the pump beam with the signal beam in a region of atmospheric space along the optical path designated as a Raman Interaction Zone (RIZ) which is selected based on its inclusion of gas and or plasma that will facilitate stimulated quantum energy absorption and emission, such that:
Stokes-shifted photons of the signal beam will be Stokes-shifted to facilitate stimulated quantum energy absorption and emission by the gas and/or plasma;
quantum energy absorption will generate an additional Stokes-shifted photon having the signal beam wavelength and the signal beam phase; and
the additional Stokes-shifted photon will amplify the signal beam.

\* \* \* \* \*